United States Patent
Zehavi et al.

(10) Patent No.: US 12,274,513 B2
(45) Date of Patent: Apr. 15, 2025

(54) DEVICES, METHODS, AND SYSTEMS FOR ROBOT-ASSISTED SURGERY

(71) Applicant: Mazor Robotics Ltd., Caesarea (IL)

(72) Inventors: Eli Zehavi, Tel-Aviv (IL); Yonatan Ushpizin, Glil Yam (IL); Ido Zucker, Tel-Aviv (IL); Adi Ess, Ramat Gan (IL)

(73) Assignee: Mazor Robotics Ltd., Caesarea (IL)

( * ) Notice: Subject to any disclaimer, the term of this patent is extended or adjusted under 35 U.S.C. 154(b) by 452 days.

(21) Appl. No.: 17/713,873

(22) Filed: Apr. 5, 2022

(65) Prior Publication Data
US 2022/0346882 A1 Nov. 3, 2022

Related U.S. Application Data

(60) Provisional application No. 63/183,486, filed on May 3, 2021.

(51) Int. Cl.
A61B 34/20 (2016.01)
A61B 34/30 (2016.01)
A61B 90/00 (2016.01)

(52) U.S. Cl.
CPC .............. *A61B 34/20* (2016.02); *A61B 34/30* (2016.02); *A61B 90/361* (2016.02); *A61B 90/39* (2016.02); *A61B 2034/2055* (2016.02); *A61B 2090/3937* (2016.02)

(58) Field of Classification Search
CPC ....... A61B 34/20; A61B 34/30; A61B 90/361; A61B 90/39; A61B 2034/2055; A61B 2090/3937
See application file for complete search history.

(56) References Cited

U.S. PATENT DOCUMENTS

| | | | |
|---|---|---|---|
| 9,526,587 B2 | 12/2016 | Zhao et al. | |
| 9,795,446 B2 | 10/2017 | DiMaio et al. | |
| 11,628,023 B2* | 4/2023 | Troxell | A61F 2/4611 |
| | | | 623/17.11 |
| 11,717,358 B2* | 8/2023 | Magaraggia | A61B 34/30 |
| | | | 600/102 |

(Continued)

FOREIGN PATENT DOCUMENTS

| EP | 3711700 | 9/2020 |
|---|---|---|
| WO | WO 2018/081136 | 5/2018 |

(Continued)

OTHER PUBLICATIONS

International Search Report and Written Opinion for International (PCT) Patent Application No. PCT/IL2022/050446, dated Aug. 26, 2022, 14 pages.

*Primary Examiner* — Jonathan T Kuo
(74) *Attorney, Agent, or Firm* — Sheridan Ross P.C.

(57) ABSTRACT

A system comprises a robotic arm in a robotic arm coordinate system, a camera in a fixed pose in a navigation coordinate system, at least one processor, and memory including instructions that when executed by the at least one processor, cause the at least one processor to determine a pose of the robotic arm within the navigation coordinate system, map the robotic arm coordinate system to the navigation coordinate system based on the pose of the robotic arm, and control, based on output of the camera, the robotic arm in the navigation coordinate system.

16 Claims, 4 Drawing Sheets

(56) References Cited

U.S. PATENT DOCUMENTS

| | | | |
|---|---|---|---|
| 11,751,948 B2* | 9/2023 | Gregerson | B25J 9/1666 |
| | | | 606/185 |
| 2020/0078097 A1* | 3/2020 | Gregerson | B25J 9/1666 |
| 2020/0229879 A1* | 7/2020 | Magaraggia | A61B 34/30 |
| 2021/0007811 A1* | 1/2021 | Troxell | A61B 34/10 |
| 2021/0391058 A1* | 12/2021 | Kostrzewski | G16H 20/40 |

FOREIGN PATENT DOCUMENTS

| | | |
|---|---|---|
| WO | WO 2020/163358 | 8/2020 |
| WO | WO 2020/185807 | 9/2020 |

* cited by examiner

DEVICES, METHODS, AND SYSTEMS FOR ROBOT-ASSISTED SURGERY

CROSS REFERENCE TO RELATED APPLICATIONS

This application claims the benefit of U.S. Provisional Application No. 63/183,486, filed on May 3, 2021, and entitled "Devices, Methods, and Systems for Robot-Assisted Surgery," which application is incorporated herein by reference in its entirety.

FIELD

The present technology generally relates to devices, systems, and methods for robot-assisted surgery.

BACKGROUND

Surgical robots may assist a surgeon or other medical provider in carrying out a surgical procedure or may complete one or more surgical procedures autonomously. Some surgeries (e.g., spinal fusion surgeries) involve placing one or more screws into bony structures of an anatomy.

SUMMARY

Example aspects of the present disclosure include:

A system comprises a robotic arm in a robotic arm coordinate system; a camera in a fixed pose in a navigation coordinate system; at least one processor; and memory including instructions that when executed by the at least one processor, cause the at least one processor to: determine a pose of the robotic arm within the navigation coordinate system; map the robotic arm coordinate system to the navigation coordinate system based on the pose of the robotic arm; and control, based on output of the camera, the robotic arm in the navigation coordinate system.

Any of the aspects herein, further comprising: a first support structure, wherein a part of the robotic arm is fixed to the first support structure at a first location on the first support structure.

Any of the aspects herein, wherein the camera is fixed to a second location on the first support structure.

Any of the aspects herein, wherein the instructions include instructions that cause the at least one processor to determine the pose of the robotic arm within the navigation coordinate system based on a known pose of the camera relative to a known pose of the robotic arm.

Any of the aspects herein, wherein the first support structure includes a patient table that supports a patient during a medical procedure.

Any of the aspects herein, further comprising a second support structure that is physically separate from the first support structure, wherein the camera is fixed to the second support structure.

Any of the aspects herein, further comprising an optical marker on the first robotic arm, wherein the instructions include instructions that cause the at least one processor to determine the pose of the robotic arm within the navigation coordinate system based on data associated with the optical marker.

Any of the aspects herein, wherein the output of the camera includes output generated based on at least one optical marker.

Any of the aspects herein, wherein the at least one optical marker includes an optical marker on a patient undergoing a medical procedure.

Any of the aspects herein, wherein the at least one optical marker further includes an optical marker on the robotic arm.

Any of the aspects herein, wherein the instructions include instructions that cause the at least one processor to generate a path within the navigation coordinate system for moving the robotic arm relative to the patient based on one or more considerations associated with a medical procedure; and control, during the medical procedure, the robotic arm based on the path.

Any of the aspects herein, wherein the one or more considerations include preventing the robotic arm from entering a line of sight between the camera and the optical marker on the patient.

Any of the aspects herein, further comprising an additional robotic arm, wherein the one or more considerations include preventing the robotic arm and the additional robotic arm from colliding with one another.

Any of the aspects herein, wherein the one or more considerations include preventing the robotic arm and the additional robotic arm from entering the line of sight between the camera and the optical marker on the patient.

A method comprises tracking a current pose of a robotic arm within a navigation coordinate system; receiving, from a camera within the navigation coordinate system, data associated with a marker on a patient; and controlling a plurality of robotic arms within the navigation coordinate system based on the data associated with the marker on the patient and the current pose of the robotic arm.

Any of the aspects herein, wherein the current pose of the robotic arm is tracked based on data associated with a marker on the robotic arm.

Any of the aspects herein, wherein the current pose of the robotic arm is tracked based on a predetermined mapping of a coordinate system of the robotic arm to the navigation coordinate system.

Any of the aspects herein, wherein the marker on the patient includes at least four elements that are distinguishable from one another within the data associated with the marker on the patient.

A device comprises at least one processor and memory including instructions that when executed by the processor cause the processor to track a current pose of a robotic arm in a navigation coordinate system; receive, from a camera within the navigation coordinate system, data associated with a marker on a patient; and control a plurality of robotic arms within the navigation coordinate system based on the data associated with the marker on the patient and the current pose of the robotic arm.

Any of the aspects herein, wherein the navigation coordinate system is a global coordinate system shared with the plurality of robotic arms.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
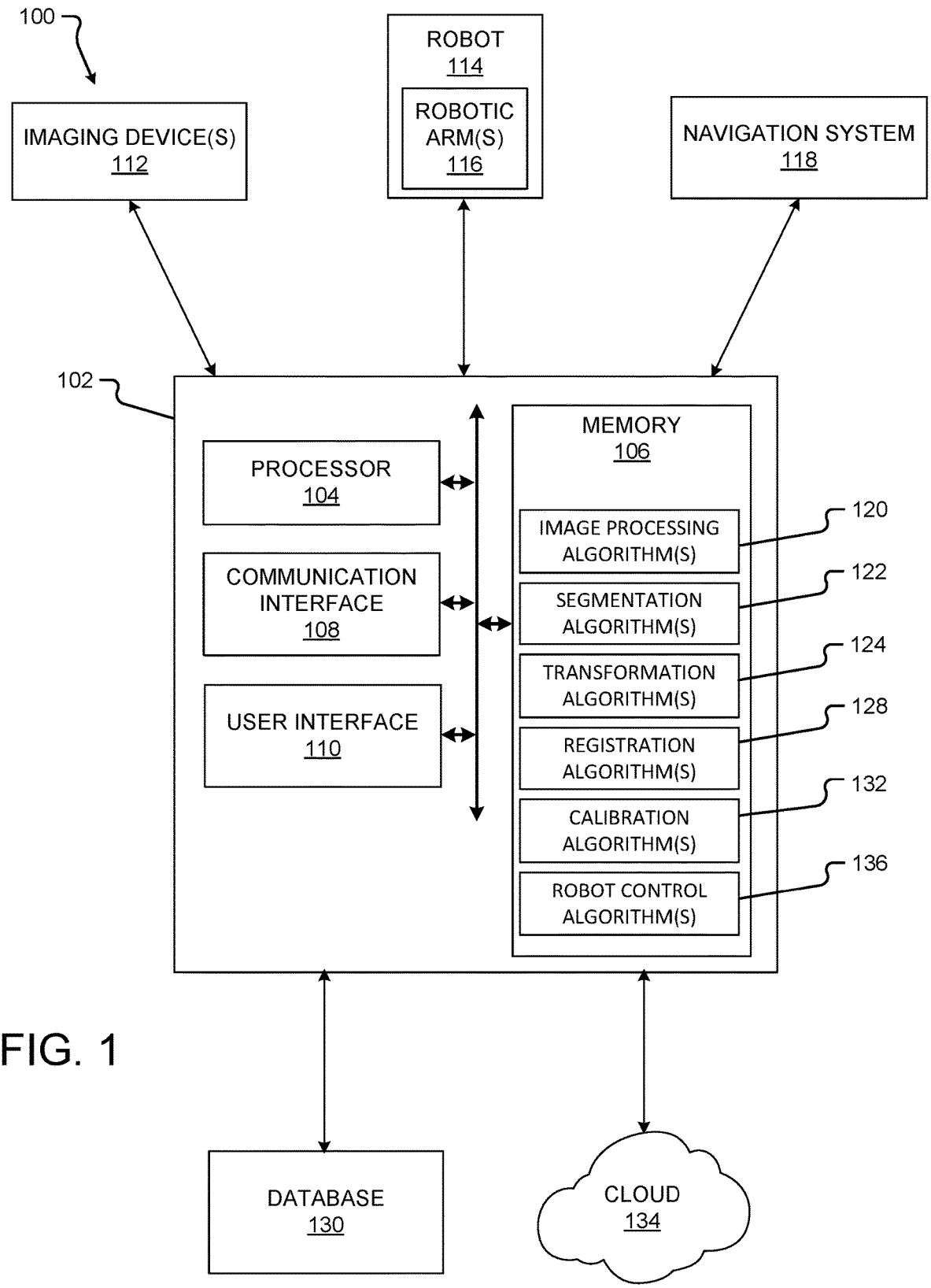
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Robot-assisted platforms are at the leading edge of innovation in spine surgery. This technology is attractive to both surgeons and patients for a number of reasons, which include increased accuracy of pedicle screw placement versus historical freehand techniques, minimally invasive procedures (e.g., small incisions and less dissection, retraction, bleeding, and infection), decreased radiation exposure to the operator versus traditional fluoroscopically assisted techniques, and/or reduced human error including fatigue, tremor, and precise repetition.

Example embodiments relate to combining a robotic arm system that performs (e.g., autonomously performs) a surgical procedure with a tracking system (e.g., optical tracking system) on a single coordinate system to achieve highly accurate performance for a variety of surgical procedures. In at least one embodiment, optical tracking elements (e.g., markers) would be placed on the robotic arm(s) to ascertain their spatial position in real time in addition to a presence of a marker that would be placed on the patient to keep the system constantly accurate relative to the anatomy. There are two options for the coordinates systems unification: a local accuracy system where the camera is placed randomly in the surgical room area (see FIG. 2 and accompanying description); and a global accuracy system where the camera is placed on the robotic system in an accurate position and the system elements will be tracked relative to the known coordinate system (see FIG. 3 and accompanying description). In the local accuracy system, the coordinate system's unification may be performed using a reference frame that allows tracking of system elements relative to a known coordinate system (e.g., a navigation coordinate system or coordinate system of the structure having the camera and robotic arm(s) attached thereto). Here, it should be appreciated that the local accuracy system may use additional hardware (e.g., markers, a support structure for the camera, image processing resource(s), and/or the like) compared to the global accuracy system because with the global accuracy system, a camera may be positioned on the same structure as the robotic arms and does not move during the procedure, which enables the global accuracy system to track everything in the navigation coordinate system and directly perform transforms to the robotic arm coordinate system. In some cases, the global coordinate system may be more accurate than the local accuracy system because the global accuracy system does not perform an additional coordinate transform as does the local accuracy system. In other words, the global accuracy system may perform a single transformation (e.g., tool to robot space) while the local accuracy system performs two transformations (e.g., tool to reference space to robot space).

Turning first to FIG. 1, a block diagram of a system 100 according to at least one embodiment of the present disclosure is shown. The system 100 may be used to assist with autonomously performing surgery or other medical procedure and/or carry out one or more other aspects of one or more of the methods disclosed herein. The system 100 comprises a computing device 102, one or more imaging devices 112, a robot 114, a navigation system 118, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 400 and 500 described herein, or of any other methods. The memory 106 may store, for example, one or more image processing algorithms 120, one or more segmentation algorithms 122, one or more transformation algorithms 124, one or more registration algorithms 128, one or more calibration algorithms 132 (see FIGS. 2-5, for example), and/or one or more robot control algorithms 136. Such instructions or algorithms may, in some embodiments, be organized into one or more applications, modules, packages, layers, or engines. The algorithms and/or instructions may cause the processor 104 to manipulate data stored in the memory 106 and/or received from or via the imaging device 112, the robot 114, the database 130, and/or the cloud 134.

The computing device 102 may also comprise a communication interface 108. The communication interface 108 may be used for receiving data or information from an external source (such as the imaging device 112, the robot 114, the navigation system 118, the database 130, the cloud 134, and/or any other system or component not part of the system 100), and/or for transmitting instructions, images, or other information to an external system or device (e.g., another computing device 102, the imaging device 112, the robot 114, the navigation system 118, the database 130, the cloud 134, and/or any other system or component not part of the system 100). The communication interface 108 may comprise one or more wired interfaces (e.g., a USB port, an ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MRI) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient. The imaging device 112 may be contained entirely within a single housing, or may comprise a transmitter/emitter and a receiver/detector that are in separate housings or are otherwise physically separated.

In some embodiments, the imaging device 112 may comprise more than one imaging device 112. For example, a first imaging device 112 may provide first image data and/or a first image, and a second imaging device 112 may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system may comprise one or more electromagnetic sensors. In various embodiments, the navigation system 118 may be used to track a position and orientation (i.e., pose) of the imaging device 112, the robot 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The robot 114 may be any surgical robot or surgical robotic system. The robot 114 may be or comprise, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112. In embodiments where the imaging device 112 comprises two or more physically separate components (e.g., a transmitter and receiver), one robotic arm 116 may hold one such component, and another robotic arm 116 may hold another such component. Each robotic arm 116 may be positionable independently of the other robotic arm, and/or the position of one robotic arm 116 may depend on or dictate a position of another robotic arm 116. The robotic arms may be controlled in a single, shared coordinate space, or in separate coordinate spaces.

The robot 114, together with the robotic arm(s) 116, may have, for example, one, two, three, four, five, six, seven, or more degrees of freedom. Further, the robotic arm(s) 116 may be positioned or positionable in any pose, plane, and/or focal point. The pose includes a position and an orientation. As a result, an imaging device 112, surgical tool, or other object held by the robot 114 (or, more specifically, by a robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm). As a result, the robotic arm(s) 116 may be accurate robotic arms, or robotic arms whose precise pose in space (relative, e.g., to a robotic arm coordinate system) is always known.

In some embodiments, reference markers (i.e., navigation markers) may be placed on the robot 114 (including, e.g., on the robotic arm 116), the imaging device 112, or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

Figure 2:
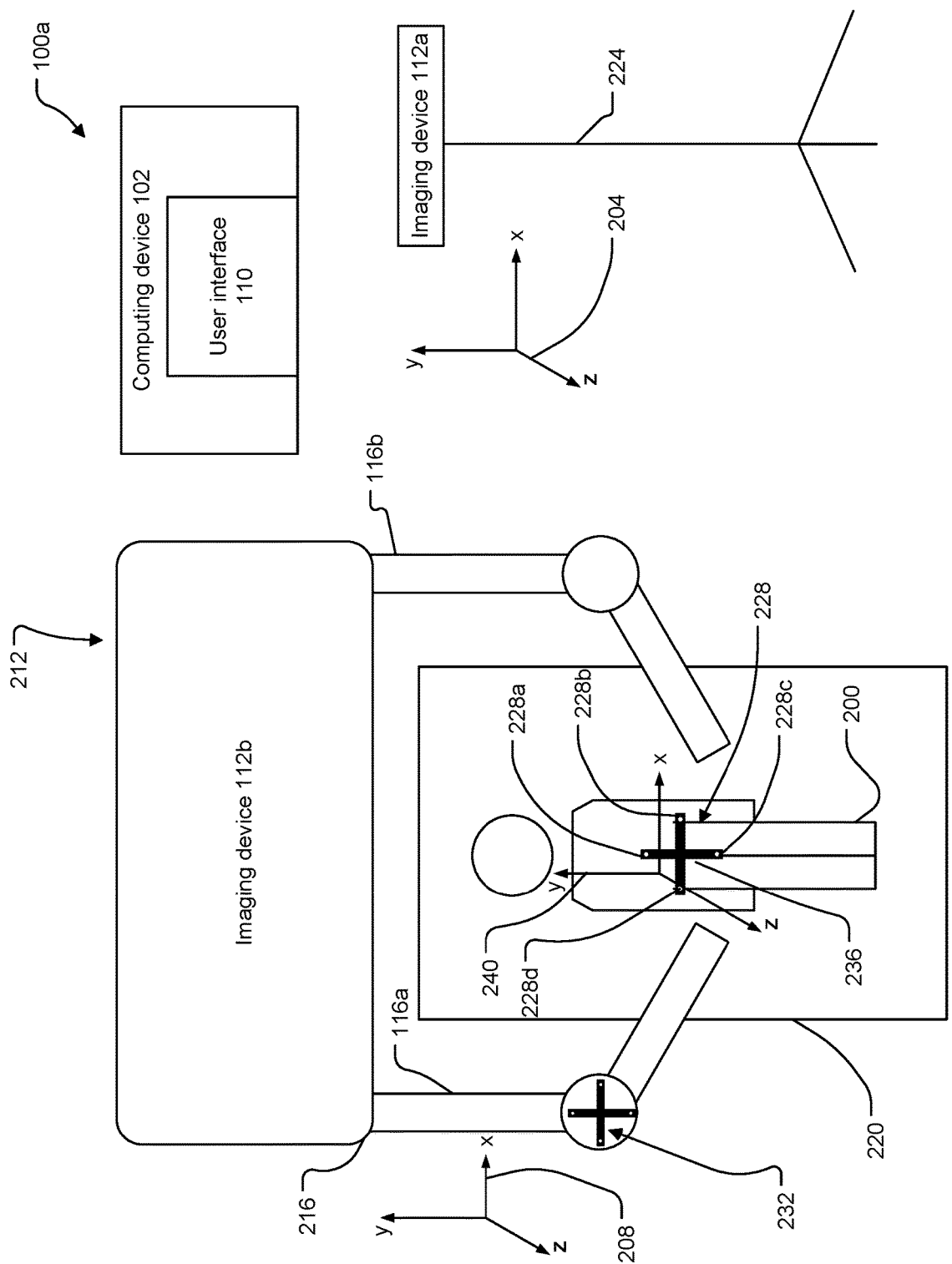
FIG. 2 illustrates various details for the system in FIG. 1 according to at least one embodiment of the present disclosure.

FIG. 2 illustrates various details for a system 100a which may be used, for example, to assist with surgery (e.g., spinal surgery) or another medical procedure on a patient 200. At least one example embodiment is directed to calibration methods for placing the robotic arms 116a and 116b into a navigation coordinate system 204 (e.g., of the navigation system 118, where the navigation coordinate system 204 may include a coordinate system of the imaging device 112a and/or coordinate system(s) of other device associated with navigating the robotic arms 116 during a procedure (e.g., a device within navigation system 118)). At least one additional example embodiment is directed to subsequent control (e.g., autonomous or semi-autonomous control) of the robotic arms 116a and 116b in the navigation coordinate system 204. Prior to calibration of the system 100a, the robotic arms 116a and 116b may exist in (e.g., be controllable relative to) their own respective coordinate systems. For example, prior to calibration, the robotic arm 116a may be in a robotic arm coordinate system 208.

FIG. 2 illustrates a computing device 102 with user interface 110, imaging devices 112a and 112b, and robotic arms 116a and 116b. Although two robotic arms 116a and 116b are shown, example embodiments related to calibration and subsequent control may be discussed with reference to only one robotic arm 116a or 116b. However, the same concepts described for one robotic arm also applies to the other robotic arm and any additional robotic arms.

The imaging device 112a may include one or more cameras (e.g., optical cameras, infrared cameras, and/or the like) for tracking various elements within the system 100a, for example, the robotic arms 116a and 116b, the patient 200, and one or more markers (discussed in more detail below). Output of the imaging device 112a may be processed by the computing device 102 to control (e.g., autonomously control) the robotic arms 116a and 116b to perform surgery on the patient 200. The imaging device 112a may be in communication with and controllable by the computing device 102.

The imaging device 112b may include an O-arm capable of 2D and/or 3D imaging. For example, the O-arm may be capable of producing x-ray images, CT images, and/or MM images of the patient 200. These images may be useful for controlling the robotic arms 116a and 116b during surgery. The imaging device 112b may be integrated with a first support structure 212. In FIG. 2, a part of the robotic arm 116a is fixed to the first support structure 212 at a first location 216 on the first support structure 212. The first support structure 212 may further include a patient table 220 that supports the patient 200 during a medical procedure. Alternatively, the patient table 220 exists as a physically separate structure from the first support structure 212. In some embodiments, the imaging devices 112a and/or 112b are considered part of the navigation system 118.

FIG. 2 further illustrates a second support structure 224 that is physically separate from the first support structure 212. In FIG. 2, the imaging device 112a is fixed to the second support structure 224. For example, the imaging device 112a is in a fixed pose on the second support structure 224. (As noted above, "pose" refers to both position and orientation of an element.)

The system 100a may include markers 228 and 232. In at least one example embodiment, the markers 228 and 232 are useful during registration or other calibration operations for the system 100a to locate the robotic arms 116a and 116b as well as the patient 200 within the navigation coordinate system 204 and/or to correlate the robotic, patient, and navigation coordinate systems together. The registered or otherwise correlated coordinate systems may then be used during a surgery using the system 100a to control the robotic arms 116a, 116b relative to the patient 200 using a single coordinate system (e.g., the navigation coordinate system). The marker 228 may be secured to location 236 on the patient 200 in a fixed pose. In this example, location 236 is on a back of the patient 200 that is receiving back surgery (e.g., spinal surgery). The marker 228 may be fixedly secured (e.g., via a pin or screw) to a pelvis or other bone of the patient 200, or secured to the patient in any other manner. Once secured to location 236, the marker 228 may be located or otherwise defined relative to a patient coordinate system 240 of the patient 200. In other words, points on or within the patient anatomy (e.g., that are relative to the surgical procedure) may be defined or definable relative to the marker 228.

The marker 232 may be adhered or otherwise affixed to the robotic arm 116a (and/or to the robotic arm 116b, although the marker 232 is not shown on the robotic arm 116b) in a fixed pose at or near a tip of the robotic arm 116a. Because each of the robotic arms 116a, 116b is affixed to the first support structure 212, and because each of the robotic arms 116a, 116b is an accurate robotic arm (e.g., a robotic arm comprising one or more sensors enabling a pose of each robotic arm 116a, 116b, relative to a robotic arm coordinate system 208, to be known at all times), only one marker 232 is needed across the robotic arms 116a, 116b and the first support structure 212 (as well as any additional robotic arms that may be affixed thereto). In other words, once a pose of one robotic arm 116 is determined (e.g., relative to a navigation coordinate system), a pose of each remaining robotic arm may be determined given that each robotic arm 116 has known relationship to each other robotic arm 116 via the first support structure 212. The use of a single fixed structure (the first fixed structure 212) to support each robotic arm 116, together with the use of accurate robotic arms, therefore beneficially simplifies the registration or other calibration process, as only one marker 228 is needed.

The markers 228 and 232 may be optical markers and include one or more elements that are detectable by the imaging device 112a. For example, marker 228 includes four elements 228a to 228d, and marker 232 may have substantially the same structure as marker 228. Each marker 228 and 232 and/or the elements of each marker 228 and 232 may include one or more light emitting diodes (LEDs), infrared emitting diodes (IREDs), reflective spheres or tape, QR codes or other geometric patterns, unique colors, and/or any other tool, device, or feature that is capable of being detected and distinguished from other elements of the system 100a by the imaging device 112a imaging device 112a.

As discussed in more detail below, the imaging device 112a may be placed anywhere in the system 100a that is within a line of sight of the markers 228 and/or 232. So long as the imaging device 112a remains in the fixed pose and the robotic arms 116a and 116b remain attached to their respective locations on the support structure 212, system 100a may be operable for multiple surgeries with a single calibration (e.g., an on-site calibration). If the imaging device 112a moves, then the system 100a may be recalibrated to ensure that the robotic arms 116a and 116b are accurately placed in the navigation coordinate system 204.

Here, it should be appreciated that additional imaging devices 112 and/or additional markers on the patient 200 and/or the robotic arm 116a (and robotic arm 116b) may be included, whether to increase the accuracy of the system 100a or otherwise. However, embodiments of the present disclosure explicitly include variations of the systems 100, 100a in which no more than two markers—one on a robotic arm 116 and one on a patient 200—are needed to correlate robotic, patient, and imaging coordinate spaces in advance of an autonomous or semi-autonomous surgical procedure (e.g., so that the robotic arms 116 may be controlled in a navigation coordinate system to interact with the patient 200 at precisely specified locations and orientations).

Figure 3:
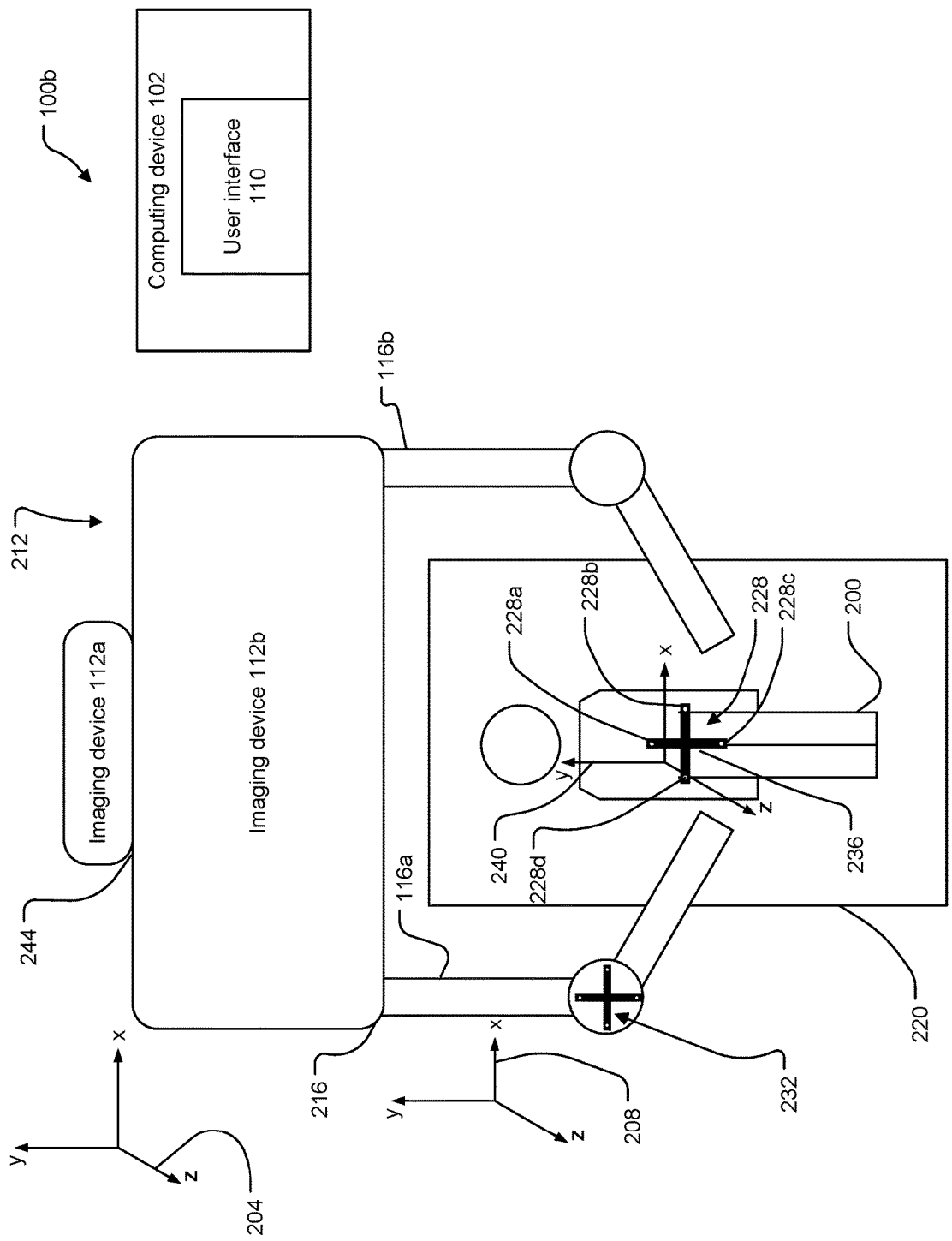
FIG. 3 illustrates various other details the system in FIG. 1 according to at least one embodiment of the present disclosure.

FIG. 3 illustrates various details for a system 100b which may be used, for example, to assist with surgery on the patient 200. The system 100b includes many of the same elements as the system 100a, and thus, a description of these elements is not repeated here. The system 100b differs from the system 100a in that the imaging device 112a is attached in a fixed and accurate pose to a second location 244 on the first support structure 212, rather than being fixed to the second support structure 224. Because the imaging device 112a and the robotic arms 116 in the system 100b are each mounted to the first support structure 212, the imaging device 112a and the robotic arms 116 are able to share a single, global coordinate system, such that no registration between separate coordinate systems corresponding to each of the imaging device 112a and the robotic arms 116 is needed. Alternatively, the imaging device 112a and the robotic arms 116 may initially (e.g., upon manufacture) have separate coordinate systems, and those coordinate systems may be registered to each other upon manufacture (and/or at normal maintenance intervals) so that, when the system 100b is used for a surgery or other medical procedure, no registration between a navigation coordinate system 204 and a robot coordinate system 208 is necessary. Indeed, so long as the imaging device 112a remains in the fixed pose and the robotic arms 116a and 116b remain attached to respective locations on the support structure 212, system 100b may be operable for multiple surgeries with a single registration or calibration (e.g., a calibration at the manufacturer or assembler of the support structure 212).

Here, it should be appreciated that since the imaging device 112a and the (accurate) robotic arms 116a and 116b are in fixed locations on the same support structure 212 and the imaging device 112a maintains a fixed pose relative to the robotic arms 116a and 116b, the robotic arms 116a and 116b and the imaging device 112a may share a global coordinate system, such that the robotic arms 116 may be controlled to assist with surgery on the patient 200 without using data (e.g., image data) associated with the marker 232. In other words, the fixed pose of the imaging device 112a relative to the (changing) poses of the robotic arms 116a and 116b at any given point in time is known, which may obviate the need for the imaging device 112a to track the marker 232 during surgery on the patient 200. However, the marker 232 may be used during an initial registration or calibration process (e.g., upon manufacture and during normal maintenance thereafter) and/or during surgery if desired. Even so, embodiments of the present disclosure explicitly include variations of the systems 100, 100b in which no more than one marker—i.e., a single marker on the patient 200—is needed to register or otherwise correlate robotic, patient, and imaging coordinate spaces in advance of an autonomous or semi-autonomous surgical procedure (e.g., so that the robotic arms 116 may be controlled in a navigation coordinate system to interact with the patient 200 at precisely specified locations and orientations, for example according to a surgical plan). In at least some such embodiments, the marker 232 is omitted entirely from the system.

The system 100 (and systems 100a and 100b discussed below) or similar systems may be used, for example, to carry out one or more aspects of any of the methods 400 and 500 described herein. The system 100 or similar systems may also be used for other purposes.

Figure 4:
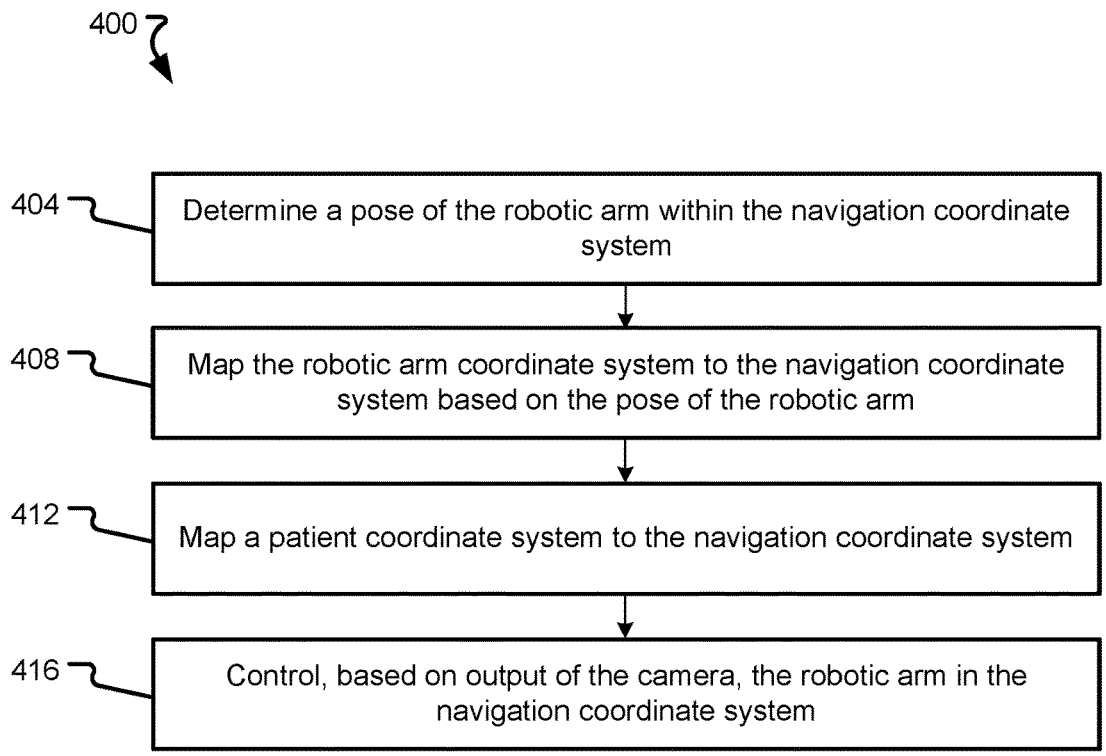
FIG. 4 is a flowchart according to at least one embodiment of the present disclosure.

FIG. 4 depicts a method 400 that may be used, for example, to calibrate the systems 100, 100a, and/or 100b and to perform surgery on a patient using the calibrated system(s).

The method 400 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 400. The at least one processor may perform the method 400 by executing instructions stored in a memory such as the memory 106. The instructions may correspond to one or more steps of the method 400 described below. The instructions may cause the processor to execute one or more algorithms, such as an image processing algorithm 120, a segmentation algorithm 122, a transformation algorithm 124, a registration algorithm 128, a calibration algorithm 132, and/or a robot control algorithm 136. FIG. 4 is discussed with reference to FIGS. 1-3.

Steps 404 and 408 below may be useful for registering or otherwise calibrating the systems 100, 100a, and/or 100b to enable control of a robotic arm using a navigation coordinate system. Meanwhile, steps 412 and 416 may be carried out after the registration or calibration operations, for example, during surgery or another medical procedure on the patient 200.

The method 400 includes determining a pose of a robotic arm within a navigation coordinate system (step 404). For example, step 404 involves determining the position and orientation (i.e., the pose) of the robotic arm 116*a* in the navigation coordinate system 204. Here, it should be appreciated any steps discussed with reference to robotic arm 116*a* may be also carried out for robotic arm 116*b* or any other additional robotic arms within the system. More specifically, because each robotic arm 116 of the system shares a common robotic arm coordinate system, registration (e.g., by completing the steps 404 and 408 of the method 400) of any one robotic arm 116 (e.g., a robotic arm 116*a* or 116*b*) is sufficient to correlate the robotic arm coordinate system to the navigation coordinate system, so as to be able to control each robotic arm 116 using the navigation coordinate system. In at least one embodiment, the pose of the robotic arm 116*a* may be determined differently for the system 100*a* and the system 100*b*.

For example, for system 100*a*, step 404 may comprise determining the pose of the robotic arm 116*a* within the navigation coordinate system 204 based on data (e.g., image data) associated with the marker 232. The data associated with the marker 232 may be based on output of the imaging device 112*a*. That is, the imaging device 112*a* senses the marker 232 (e.g., by capturing light waves reflecting off of or emitted by the marker 232 and/or the elements thereof) and generates image data associated with the marker 232. The computing device 102 or another processor may then be used to determine a pose of the marker 232 in the navigation coordinate system 204 based on the relative position of the elements thereof within the image data, and information about a pose of the marker 232 relative to a pose of the robotic arm 116*a* may be used to determine a pose of the robotic arm 116 relative to the navigation coordinate system 204. In other words, the computing device 102 uses the sensed pose of the marker 232 to calculate (or estimate) an actual pose of the robotic arm 116*a*.

Here, it should be appreciated that the image data associated with the marker 232 is useful for calibrating the system 100*a* (e.g., by registering the navigation coordinate system 204 to the robotic arm coordinate system 208) because the pose of the imaging device 112*a* relative to the pose of the robotic arm 116*a* may not be initially known, for example, if step 404 is carried out after moving the imaging device 112*a* on the support structure 224 within the system 100*a*. Thus, the marker 232 provides information on the pose of the robotic arm 116*a* as sensed by the imaging device 112*a*, which the computing device 102 uses to determine the current pose of the robotic arm 116*a*.

For system 100*b*, step 404 may comprise determining the pose of the robotic arm 116*a* within the navigation coordinate system 204 based on a known pose of the robotic arm 116*a* within the robotic arm coordinate system 208. The known pose of the robotic arm 116*a* in the robotic arm coordinate system 208 may be determined based on knowledge associated with the structure (e.g., support structure 212) to which the imaging device 112*a* and the robotic arm 116*a* are mounted or fixed. For example, at the manufacturing or assembly stage for system 100*b*, the imaging device 112*a* and the robotic arm 116*a* may be mounted to the support structure 212 with known poses and/or with known relative poses. In this case, determining the pose of the robotic arm 116*a* within the navigation coordinate system 204 may include the computing device 102 retrieving or receiving information (e.g., from memory or user input) about the known poses and/or the known relative poses of the robotic arm 116*a* and the imaging device 112*a* within the navigation coordinate system 204. For example, the robotic arm 116*a* includes a portion fixed to location 216 and the robotic arm 116*a* may be assembled in or controlled to be in a predetermined pose related to the imaging device 112*a* when mounted to the support structure 212 at location 216. The known location 216, the known pose of the imaging device 112*a*, and/or the predetermined pose of the robotic arm 116*a* may be used to determine the pose of the robotic arm 116*a* in the navigation coordinate system 204. In other words, where the imaging device 112*a* and the robotic arms 116 are mounted to a common support structure (e.g., the first support structure 212), a pose of the robotic arm 116*a* relative to the navigation coordinate system 204 may be determined without using image data generated by the imaging device 112*a*.

Thereafter, the method may proceed to operation 408. Example embodiments are not limited to the methods described above for performing step 404 in system 100*b*. For example, in at least one embodiment, the imaging device 112*a* may determine the pose of the robotic arm 116*a* within the navigation coordinate system 204 based on image data associated with the marker 232 in the same manner as that discussed above for system 100*a*.

The method 400 may include mapping or otherwise registering a robotic arm coordinate system to the navigation coordinate system (or mapping or otherwise registering the navigation coordinate system to the robotic arm coordinate system, which achieves the substantially same result) based on the pose of the robotic arm (step 408). For example, for each system 100*a* and 100*b*, step 408 includes mapping or otherwise registering the robotic arm coordinate system (or robotic arm frame of reference) 208 to the navigation coordinate system (or camera frame of reference) 204 based on the pose of the robotic arm 116*a* determined in step 404. The mapping may additionally utilize information about a pose of the robotic arm 116*a* in the robotic arm coordinate system 208, such that specific points in the navigation coordinate system 204 may be aligned with specific points in the robotic arm coordinate system 208. The mapping may involve determining a suitable transformation algorithm 124 to transform any given coordinates in one coordinate system (e.g., the robotic arm coordinate system 208) into corresponding coordinates in the other coordinate system (e.g., the navigation coordinate system 204) so that the robotic arm 116*a* is controllable within the camera coordinate system 204. For example, a transformation algorithm 124 may employ a transformation matrix based on the known poses of the imaging device 112*a* and robotic arm 116*a* to describe an actual or planned pose of the robotic arm 116*a* in the navigation coordinate system 204.

The method 400 also includes operation 412 that maps a patient coordinate system to the navigation coordinate system (or that maps the navigation coordinate system to the patient coordinate system, which achieves substantially the same result). The mapping is based on image data corresponding to the marker 228, as well as information about a pose of the marker 228 relative to a coordinate system corresponding to the patient 200. The latter information may be or comprise, for example, one or more images (captured by the imaging device 112*a* or another imaging device 112) that depict the marker 228 as well as relevant anatomy of the patient 200 (e.g., anatomy of the patient 200 that is relevant to a surgery or other medical procedure to be carried out on the patient). The mapping may comprise, for example, determining a pose of the marker 228 in the navigation coordinate system 204, which may be accomplished in the same manner as determining a pose of the marker 232 in the navigation coordinate system 204 in connection with the step 404, as described above. The mapping may further comprise utilizing the determined pose of the marker 228 in the navigation coordinate system 204, together with information about a pose of the marker 228 relative to the coordinate system of the patient 200, to map or otherwise register the patient coordinate system to the navigation coordinate system 204. This, too, may be accomplished in a manner similar to that described above in connection with the step 408 for mapping the robotic arm coordinate system 208 to the navigation coordinate system 204. Once both the robotic arm coordinate system and the patient coordinate system have been mapped to the navigation coordinate system, the robotic arms 116 may be precisely controlled relative to the patient 200 using the navigation coordinate system. Moreover, if the patient 200 moves, the imaging device 112a can detect such movement, and the robotic arms 116 may be precisely controlled in light of the current, post-movement patient pose. Embodiments of the present disclosure therefore beneficially avoid the need for a re-registration of a patient coordinate space to one or both of a navigation coordinate system and/or a robotic arm coordinate system resulting from movement (whether expected or unexpected) of the patient.

The mapping of the patient coordinate system to the navigation coordinate system may be accomplished without any markers other than the marker 228. In other words, the step 412 may be accomplished with only a single marker attached to the patient.

The method 400 includes controlling, based on output of the camera, the robotic arm in the navigation coordinate system (step 416). For example, in both systems 100a and 100b, the method 400 controls (e.g., autonomously or semi-autonomously controls) the robotic arm 116a in the navigation coordinate system 204 based on image data generated by the imaging device 112a. The robotic arm 116a (and any other robotic arms 116 secured to the first support structure 212) may be controlled, in the navigation coordinate system 204, to assist with surgery on the patient 200. As discussed in more detail with reference to FIG. 5, the output of the imaging device 112a may include data (e.g., image data) associated with the marker 228 and/or the marker 232.

For example, in system 100a, the output of the imaging device 112a includes data associated with the marker 228 on the patient 200 and data associated with the marker 232 on the robotic arm 116a. For system 100b, the output of the camera 112 may include data associated with the marker 228 on the patient 200 and not data associated with the marker 232 (because the imaging device 112a and the robotic arm 116a share a common coordinate system, such that the marker 232 is not needed). Example embodiments are not limited thereto and the output of the imaging device 112a for system 100b may include substantially the same type of data as the output of the imaging device 112a for system 100a.

In any event, step 416 may include one or more sub-steps for controlling the robotic arms 116a and 116b (and any other robotic arms 116) to assist with surgery or another medical procedure on the patient 200. For example, step 416 may include generating a path within the navigation coordinate system 204 for moving the robotic arm 116a and/or robotic arm 116b relative to the patient 200 based on one or more considerations associated with the medical procedure, and controlling, during the medical procedure, the robotic arm 116a and/or robotic arm 116b based on the path.

In at least one example embodiment, the one or more considerations include preventing the robotic arm 116a and/or robotic arm 116b from entering a line of sight between the imaging device 112a and the optical marker 228 on the patient 200. Preventing the robotic arm(s) from blocking the camera's 112a line of sight to the optical marker 228 may be useful for improving the accuracy and speed of the procedure since an obstructed line of sight may prevent accurate determination of a pose of one or more robotic arms 116 relative to the patient 200, and therefore necessitate a pause of the procedure.

In at least one example embodiment, the one or more considerations include preventing the robotic arm 116a and at least one additional robotic arm 116b from colliding with one another and/or with other elements of the system 100, thereby improving the overall safety and effectiveness of the medical procedure. In such embodiments, any physical obstacles positioned within the working volume of the robotic arms 116 (e.g., surgical tools, the surgeon herself) may be identified (whether by the imaging device 112a, input provided via a user interface 110, or in any other way) and taken into consideration when any movement of the robotic arms 116 is planned and/or effected. In such embodiments, the line of sight from the imaging device 112a to the optical marker 228 may be coded or otherwise treated as a physical obstacle within the work volume of the robotic arms 116, and any path planning algorithm used to determine a movement path to enable a robotic arm 116 to move from a current pose to a planned pose may be configured to avoid "contact" with the line of sight just as actual physical contact with any other obstacle would be avoided.

The present disclosure encompasses embodiments of the method 400 that comprise more or fewer steps than those described above, and/or one or more steps that are different than the steps described above. In addition, one or more steps of the method 400 may be performed in a different order or performed simultaneously.

Figure 5:
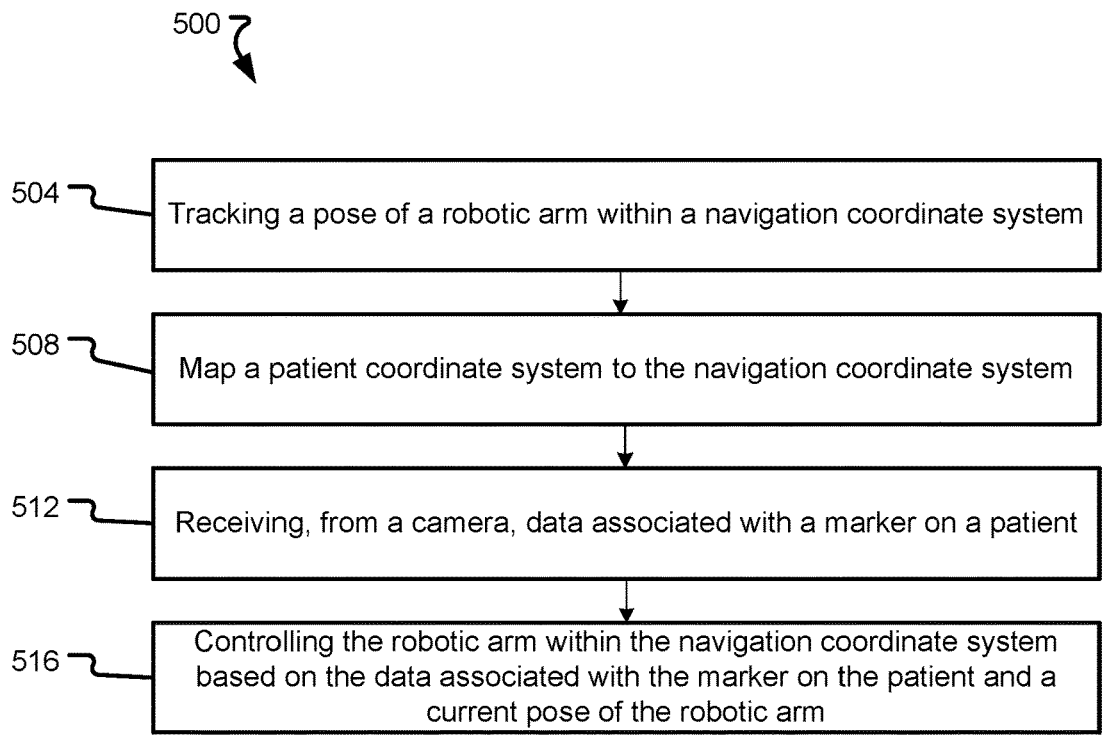
FIG. 5 is a flowchart according to at least one embodiment of the present disclosure.

FIG. 5 depicts a method 500 that may be used, for example, to perform a medical procedure on a patient using one or more robotic arms that have been mapped to a coordinate system of a camera.

The method 500 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 500. The at least one processor may perform the method 500 by executing instructions stored in a memory such as the memory 106. The instructions may correspond to one or more steps of the method 500 described below. The instructions may cause the processor to execute one or more algorithms, such as an image processing algorithm 120, a segmentation algorithm 122, a transformation algorithm 124, a registration algorithm 128, a calibration algorithm 132, and/or a robot control algorithm 136. FIG. 5 is discussed with reference to FIGS. 1-4.

Here, it should be appreciated that FIG. 5 illustrates steps that may be performed during surgery or other medical procedure on the patient 200.

The method 500 includes tracking a current pose of a robotic arm within a navigation coordinate system (step 504). In some embodiments, the tracking may comprise determining an initial pose of the robotic arm 116a within the navigation coordinate system 204 and thereafter tracking the current pose of the robotic arm 116a during surgery or another medical procedure. In such embodiments, the initial pose of the robotic arm 116a may be determined in the same manner as that described above in step 404. For example, in system 100a, the initial pose of the robotic arm 116a may be determined based on image data associated with the marker 232 which the computing device 102 uses to calculate or estimate the initial pose of the robotic arm 116a in the navigation coordinate system 204. Meanwhile, in system 100b, the initial pose of the robotic arm 116a may be determined based on a known relative pose of the imaging device 112a and the robotic arm 116a (or any other robotic arm 116), as well as on sensed information about an actual pose of the robotic arm 116a. In this case, the initial pose of the robotic arm 116 determined in step 504 may be substantially the same as the pose of the robotic arm 116a used for calibrating the system 100b in operations 404 and 408.

In other embodiments, the step 504 does not involve determining an initial pose of the robotic arm 116a within the navigation coordinate system 204, but instead simply uses image data (in the system 100a) or sensed robotic arm pose data (in the system 100b, where the imaging device 112a and the robotic arms 116 share a global coordinate system) to track a pose of the robotic arm 116a, relying on an existing registration between the robotic arm coordinate system 208 and the navigation coordinate system 204.

After determining the initial pose of the robotic arm 116a or once a registration between the navigation coordinate system 204 and the robotic arm coordinate system 208 is complete, the current pose of the robotic arm 116a may be tracked throughout the surgery or other medical procedure. For example, in system 100a, the pose of the robotic arm 116a is tracked, in the navigation coordinate system 204, based on the data associated with marker 232. In this case, the computing device 102 uses the sensed pose of the marker 232 (as sensed by the imaging device 112a) to calculate or estimate an actual pose of the robotic arm 116a based on the sensed pose of the marker 232. In system 100b, the pose of the robotic arm 116a may be tracked without the data associated with the marker 232, using known information (e.g., information obtained from sensors monitoring the robotic arm 116a) about a pose of the accurate robotic arm. More specifically, in the system 100b, the robotic arms 116 and the imaging device 112a may share a common, global coordinate system. As a result, the robotic arm 116a may be readily tracked by the computing system 102 within that common coordinate system (based on, for example, data obtained from sensors configured to monitor a pose of the robotic arm 116a). Alternatively, where the robotic arms 116 and the imaging device 112a do not share a common coordinate system, and the separate robotic and navigation coordinate systems were registered to one another (for example, upon manufacture of the system or during regular maintenance), the computing device 102 tracks the robotic arm 116a within the navigation coordinate system 204. In other words, in such embodiments the current pose of the robotic arm 116a is tracked based on a predetermined mapping of a coordinate system 208 of the robotic arm 116a to the navigation coordinate system 204. In system 100b, the pose of the robotic arm 116a may be additionally or alternatively tracked based on the data associated with the marker 232 if desired.

The method 500 also comprises mapping a patient coordinate system to the navigation coordinate system (step 508). The step 508 is the same as, or substantially similar to, the step 412 of the method 400, described above. In at least one embodiment, operation 508 maps the navigation coordinate system to the patient coordinate system, which achieves the substantially same result as mapping the patient coordinate system to the navigation coordinate system.

The method 500 includes receiving, from a camera, data associated with a marker on a patient (step 512). For example, the imaging device 112a produces the image data associated with marker 228 on the patient 200 by sensing/tracking (e.g., capturing images of) the marker 228 during surgery or another medical procedure. The data associated with the marker 228 may be received and processed by the computing device 102 (e.g., received and processed at the same time as tracking the robotic arm in step 504). Step 512 may occur for both system 100a and 100b because the marker 228 is attached to a potentially non-stationary patient 200. Thus, the imaging device 112a may be used to generate image data regarding the marker 228, and the computing device 102 or any other processor may be used to evaluate the image data and monitor (e.g., continuously monitor) the marker 228 to detect any patient movement or other disruption.

The method 500 includes controlling the robotic arm within the navigation coordinate system based on the data associated with the marker 228 and a current pose of the robotic arm (516). For example, the robotic arm 116a is controlled within the navigation coordinate system 204 based on the data associated with the marker 228 received in operation 512 and based on a current pose of the robotic arm 116a as determined in the tracking step 504. Step 516 may be carried out in the same or similar fashion as step 416 from FIG. 4.

The step 516 may also comprise controlling one or more robotic arms 116 based on a surgical plan. For example, the step 516 may comprise controlling the robotic arms 116 to move to a precise position relative to the patient 200, using image data generated by the imaging device 112a to ensure accurate movement of the robotic arms 116 relative to the patient 200, to accomplish a surgical task specified in a surgical plan. Such a surgical plan may be received by or at a processor 104 or any other processor from and/or via, for example, a communication interface 108, a user interface 110, a database 130, and/or a network such as the cloud 134.

The present disclosure encompasses embodiments of the method 500 that comprise more or fewer steps than those described above, and/or one or more steps that are different than the steps described above. In addition, one or more steps of the method 500 may be performed in a different order or performed simultaneously.

Embodiments of the present disclosure beneficially reduce the number of markers (such as, for example, the markers 228 and 232 described herein) needed for tracking a pose of a plurality of robotic arms as well as a patient during a surgery or other medical procedure. For example, some embodiments of the present disclosure enable registration of a navigation coordinate system, a robotic arm coordinate system corresponding to a plurality of robotic arms, and a patient coordinate system using only one marker on one robotic arm of a plurality of robotic arms, and only one marker on a patient. Other embodiments of the present disclosure enable registration of a global coordinate system shared by a plurality of robotic arms and a camera mounted in an accurate pose relative to the plurality of robotic arms, and a patient coordinate system, using only a single marker fixedly secured to a patient. Moreover, embodiments of the present disclosure beneficially enable the positioning of a camera anywhere in an operating room having a line of sight to a marker on a patient and a marker on one robotic arm of a plurality of robotic arms, or alternatively the use of a camera mounted to the same support structure as a plurality of robotic arms, thus avoiding the need for a separate camera support structure and reducing clutter in the operating room.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system comprising:
   a robotic arm in a robotic arm coordinate system;
   a camera in a fixed pose in a navigation coordinate system;
   at least one processor; and
   memory including instructions that when executed by the at least one processor, cause the at least one processor to:
   determine a pose of the robotic arm within the navigation coordinate system;
   map the robotic arm coordinate system to the navigation coordinate system based on the pose of the robotic arm; and
   control, based on output of the camera, the robotic arm in the navigation coordinate system,
   wherein the output of the camera includes output generated based on at least one optical marker including an optical marker on a patient,
   wherein the instructions include instructions that cause the at least one processor to:
   generate a path within the navigation coordinate system for moving the robotic arm relative to the patient based on one or more considerations associated with a medical procedure, wherein the one or more considerations include preventing the robotic arm from entering a line of sight between the camera and the optical marker on the patient; and
   control, during the medical procedure, the robotic arm based on the path.

2. The system of claim 1, further comprising:
   a first support structure, wherein a part of the robotic arm is fixed to the first support structure at a first location on the first support structure.

3. The system of claim 2, wherein the camera is fixed to a second location on the first support structure.

4. The system of claim 3, wherein the instructions include instructions that cause the at least one processor to:
   determine the pose of the robotic arm within the navigation coordinate system based on a known pose of the camera relative to a known pose of the robotic arm.

5. The system of claim 2, wherein the first support structure includes a patient table that supports the patient during the medical procedure.

6. The system of claim 2, further comprising:
   a second support structure that is physically separate from the first support structure, wherein the camera is fixed to the second support structure.

7. The system of claim 6, further comprising:
   an optical marker on the robotic arm, wherein the instructions include instructions that cause the at least one processor to determine the pose of the robotic arm within the navigation coordinate system based on data associated with the optical marker on the robotic arm.

8. The system of claim 1, wherein the at least one optical marker further includes an optical marker on the robotic arm.

9. The system of claim 1, further comprising:
   an additional robotic arm, wherein the one or more considerations include preventing the robotic arm and the additional robotic arm from colliding with one another.

10. The system of claim 9, wherein the one or more considerations include preventing the robotic arm and the additional robotic arm from entering the line of sight between the camera and the optical marker on the patient.

11. A method, comprising:
    tracking a current pose of a robotic arm within a navigation coordinate system;
    receiving, from a camera within the navigation coordinate system, data associated with a marker on a patient; and
    controlling a plurality of robotic arms within the navigation coordinate system based on the data associated with the marker on the patient and the current pose of the robotic arm, wherein controlling the plurality of robotic arms within the navigation coordinate system includes:
    generating a path within the navigation coordinate system for moving the robotic arm relative to the patient based on one or more considerations associated with a medical procedure, wherein the one or more considerations include preventing the robotic arm from entering a line of sight between the camera and the marker on the patient; and
    controlling, during the medical procedure, the robotic arm based on the path.

12. The method of claim 11, wherein the current pose of the robotic arm is tracked based on data associated with a marker on the robotic arm.

13. The method of claim 11, wherein the current pose of the robotic arm is tracked based on a predetermined mapping of a coordinate system of the robotic arm to the navigation coordinate system.

14. The method of claim 11, wherein the marker on the patient includes at least four elements that are distinguishable from one another within the data associated with the marker on the patient.

15. A device, comprising:
at least one processor; and
memory including instructions that when executed by the processor cause the processor to:
- track a current pose of a robotic arm in a navigation coordinate system;
- receive, from a camera within the navigation coordinate system, data associated with a marker on a patient; and
- control a plurality of robotic arms within the navigation coordinate system based on the data associated with the marker on the patient and the current pose of the robotic arm, wherein controlling the plurality of robotic arms within the navigation coordinate system includes:
- generating a path within the navigation coordinate system for moving the robotic arm relative to the patient based on one or more considerations associated with a medical procedure, wherein the one or more considerations include preventing the robotic arm from entering a line of sight between the camera and the marker on the patient; and
- controlling, during the medical procedure, the robotic arm based on the path.

16. The device of claim 15, wherein the navigation coordinate system is a global coordinate system shared with the plurality of robotic arms.

\* \* \* \* \*